United States Patent
Fischer et al.

(10) Patent No.: US 8,372,799 B2
(45) Date of Patent: Feb. 12, 2013

(54) REVERSE PROTEIN

(75) Inventors: Bernhard Fischer, Vienna (AT); Rudolf Lucas, Aartselaar (BE)

(73) Assignee: Apeptico Forschung und Entwicklung GmbH, Vienna (AT)

( * ) Notice: Subject to any disclaimer, the term of this patent is extended or adjusted under 35 U.S.C. 154(b) by 121 days.

(21) Appl. No.: 12/747,741

(22) PCT Filed: Dec. 12, 2008

(86) PCT No.: PCT/AT2008/000447
§ 371 (c)(1),
(2), (4) Date: Aug. 10, 2010

(87) PCT Pub. No.: WO2009/073908
PCT Pub. Date: Jun. 18, 2009

(65) Prior Publication Data
US 2011/0021411 A1 Jan. 27, 2011

(30) Foreign Application Priority Data
Dec. 12, 2007 (AT) .............................. A 2015/2007

(51) Int. Cl.
*A61K 38/12* (2006.01)
*A61K 38/19* (2006.01)
*C07K 14/525* (2006.01)

(52) U.S. Cl. ............ 514/1.1; 514/1.5; 514/1.6; 514/1.7; 514/870; 530/317; 930/144

(58) Field of Classification Search ........................ None
See application file for complete search history.

(56) References Cited

U.S. PATENT DOCUMENTS
4,894,439 A 1/1990 Dorin et al.
2003/0105021 A1* 6/2003 Lucas et al. ................... 514/13

FOREIGN PATENT DOCUMENTS
DE 3841759 A1 6/1990
EP 1 452 868 A2 9/2004
WO 90/06945 6/1990
WO 00/09149 A 2/2000

OTHER PUBLICATIONS

Bowie et al. Deciphering the message in protein sequences: tolerance to amino acid substitutions. Science, (Mar. 16, 1990) 247 (4948) 1306-10.*

Ngo et al., In the Protein Folding Problem and Tertiary Structure Prediction, Merz and Le Grand (Eds), Aug. 1994, Springer Verlag, pp. 433 and 492-495.*
Michael A. Narachi, Eet al "Role of Single Disulfide in Recombinant Human Tumor Necrosis Factor-a" The Journal fo Biological Chemistry, vol. 262, No. 27, Sep. 25, 1987, pp. 13107-13110.
Database Geneseq Target Molecule binding peptide #49; , Nov. 18, 2004; XP002516879 retrieved from EBI accession No. GSN: ADR75465 Database accession No. ADR75465.
E.A. Carswell, et al. "An endotoxin-induced serum factor that causes necrosis of tumors" Proc. Nat. Acad. Sci. USA, vol. 72, No. 9, pp. 3666-3670, Sep. 1957, Immunology.
Bharat B. Aggarwal, et al. "Primary Structure of Human Lymphotoxin Derived from 1788 Lymphoblastoid Cell Line" The Journal of Biological Chemistry, vol. 260, Issue Feb. 25, pp. 2334-2344, 1985 USA.
Glen E. Nedwin, et al. "Human lymphotoxin and tumor necrosis factor genes: structure, homology and chromosomal localization" Nucleic Acids Research, vol. 13, No. 17, 1985, pp. 6361-6373.
Pierre-François Piguet, et al "Tumor Necrosis Factor/Cachectin is an Effector of Skin and Gut Lesions of the Acute Phase of Graft-vs.-Host Disease" J. Exp. Med. vol. 166, Nov. 1987 pp. 1280-1289.
Marusa Hribar, et al. "The lectin-like domain of tumor necrosis factor-α increases membrane conductance in mircrovascular endothelial cells and peritoneal macrophages" Eur. J. Immunol. 1999, 29:3105-3111.
Clemens Braun, et al "Dichotomal Role of TNF in Experimental Pulmonary Edema Reabsorption" J. Immunol. 2005; 175;3402-3408.
Norimasa Fukuda, et al. "Mechanisms of TNF-α stimulation of amiloride-sensitive sodium transport across alveolar epithelium" Am J Physiol Lung Cell Mol Physiol 280:L1258-L1265, 2001.
M. T. Clunes, et al. "A glucocorticoid-incuded NA+ conductance in human airway epithelial cells identified by perforated patch recording" J Physiol 557.3 (2004) pp. 809-813.
Ahmet Feridun Isik, et al. "A new agent for treatment of acute respiratory distress syndrome: thymoquinone. An experimental study in a rat model" European Journal of Cardio-Thoracic Surgery 28 (2005) 301-305.

* cited by examiner

*Primary Examiner* — David Romeo
(74) *Attorney, Agent, or Firm* — Workman Nydegger

(57) ABSTRACT

A protein which is composed N-terminally of one or several C-terminal parts of the amino acid sequence of the mature tumor necrosis factor and C-terminally of one or several N-terminal parts of the amino acid sequence of the mature tumor necrosis factor, which activates epithelial ion channels and improves the lung function and which can be used for the manufacture of medicaments for the treatment of diseases associated with the lung function, such as oedemas.

14 Claims, 3 Drawing Sheets

REVERSE PROTEIN

The present invention relates to a reverse protein, namely a tumour necrosis factor protein (polypeptide) which is composed N-terminally of one or several C-terminal parts of the amino acid sequence of the mature tumour necrosis factor (TNF) and C-terminally of one or several N-terminal parts of the amino acid sequence of the TNF, whereby the protein can be used as a medicament, e.g., for activating epithelial ion channels, for improving the lung function as well as for treating oedemas such as pulmonary oedemas.

The fluid transport through cell layers and tissue is primarily based on an osmotic gradient by an active vectorial ion transport, e.g., sodium transport. It is accomplished mainly by strictly regulated and vitally important ion channels such as, e.g., the epithelial sodium channel complex (ENaC). Water passively follows this gradient, inter alia, through special water channels such as the water channel Aquaporin V. For lung tissue it is known that, basolaterally on the pumping cells, Na+/K+ ATPases drive the vectorial transport of sodium into the interstice and finally of ions into the lymph and blood vessels. Thus, said transport is active and occurs independently of the transpulmonary pressure and the alveolar protein concentration.

An oedema is a pathological accumulation of fluid in an organ such as, e.g., in the lungs, but also in the brain or in the skin. An oedema in the lungs is called a pulmonary oedema. The pulmonary oedema is mostly based on an imbalance between fluid extravasation and fluid resorption. Very often, the permeability of the lung tissue is also damaged so that an increased fluid supply occurs and the fluid accumulates in the pulmonary alveoli.

Such a permeability defect as a result of a lack of return transport of fluid from the pulmonary alveoli into the interstice is particularly significant for an Acute Lung Injury, ALI, or for the Acute Respiratory Distress Syndrome, ARDS, or for the Severe Acute Respiratory Syndrome (SARS), for pneumonia and for multi-organ failure. However, the permeability defect also plays a part in other lung diseases such as respiration-induced lung injuries, lung transplants, transfusion-associated lung injuries, therapeutical administration of IL-2 or asthma.

As a result of an increased fluid accumulation in the tissue or organ, e.g., in the lungs, the required gas exchange is impeded or completely restricted. No oxygen from the breathing air reaches the blood so that life-threatening organ damages may occur due to oxygen deficiency.

There is no general standard therapy for the treatment of the permeability oedema. It is generally attempted to give artificial respiration to patients having pulmonary oedemas in order to ensure the supply of oxygen into the blood and thus into the organs.

Individual peptides derived from the TNF are known from DE 38 41 759.

Carswell et al. in Proc. Natl. Acad. Sci. USA 72, 3666, 1975, have reported that the serum of animals treated with endotoxin, which previously had been infected with the mycobacterial strain Calmette-Guerin (BCG), caused haemorrhagic necrosis in different tumours in mice. This activity was attributed to the tumour necrosis factor (TNF). TNF also shows a cytostatic or cytotoxic in vitro activity against a plurality of transformed cell lines, whereas normal human and animal cell lines are not affected by this (M. R. Ruff et al, Lymphokines, Vol. II, Academic Press Inc., New York, 1981, pp 235-275). The biochemical characterization and the gene for human TNF has already been described (D Pennica et al, Nature 312, 724, 1984; Aggarwal, B. B. et al, J. Biol. Chem. 260, 2334-2345, 1985; Nedwin, G. E. et al, Nucl. Acids Res. 13, 6361, 1985).

It has been possible to derive the following protein structure for the human mature tumour necrosis factor (TNF) from these data:

(NH$_2$)Val Arg Ser Ser Ser Arg Thr Pro Ser Asp Lys Pro Val Ala His Val Val Ala Asn Pro Gln Ala Glu Gly Gln Leu Gln Trp Leu Asn Arg Arg Ala Asn Ala Leu Leu Ala Asn Gly Val Glu Leu Arg Asp Asn Gln Leu Val Val Pro Ser Glu Gly Leu Tyr Leu Be Tyr Ser Gln Val Leu Phe Lys Gly Gln Gly Cys Pro Ser Thr His Val Leu Leu Thr His Thr Ile Ser Arg Ile Ala Val Ser Tyr Gln Thr Lys Val Asn Leu Leu Ser Ala Ile Lys Ser Pro Cys Gln Arg Glu Thr Pro Glu Gly Ala Glu Ala Lys Pro Trp Tyr Glu Pro Be Tyr Leu Gly Gly Val Phe Gln Leu Glu Lys Gly Asp Arg Leu Ser Ala Glu Ile Asn Arg Pro Asp Tyr Leu Asp Phe Ala Glu Ser Gly Gln Val Tyr Phe Gly Be Ile Ala Leu(COOH) (SEQ ID NO:4)

Furthermore, the TNF-gene of cattle, rabbit and mouse has been described (Goeddel D. V. et al., Cold Spring Harbor Symp. Quant. Biol. 51, 597, 1986).

Besides its cytotoxic properties, TNF, amongst others, plays a major part in inflammatory reactions (J. W. Larrick et al, Pharmac. Res. Vol. 5, No. 3, 129-139, 1988). In an animal model, it has been possible to demonstrate the involvement of TNF in septic shock (Torti F. M. et al, Science 229, 867-869, 1985) and in the graft versus host disease (Piguet, P F et al, J. Exp. Med. 166, 1280, 1987).

It is known from biochemical examinations that the human TNF is made up of different structural elements as listed in TABLE 1:

TABLE 1

| Structural element | Position of amino acids |
| --- | --- |
| β-STRAND 1 | 30-32 |
| β-STRAND 2 | 45-49 |
| β-STRAND 3 | 54-71 |
| β-STRAND 4 | 76-83 |
| β-STRAND 5 | 85-87 |
| β-STRAND 6 | 91-98 |
| β-STRAND 7 | 101-103 |
| U-Turn 8 | 104-106 |
| β-STRAND 9 | 107-109 |
| β-STRAND 10 | 113-126 |
| β-STRAND 11 | 131-137 |
| α-HELIX 12 | 139-141 |
| β-STRAND 13 | 147-153 |

In Lucas R et al, Science (1994) Vol. 263. no. 5148, pp. 814-817, a peptide is described which has been derived from region Ser(99) to Glu(116) of the TNF and which is suggested for the treatment of oedemas. Said peptide is also the subject matter of WO 00/09149.

However, in order to render this peptide of WO 00/09149 usable, position Pro(100) had to be replaced artificially by the amino acid cysteine and position Cys(101) had to be replaced artificially by the amino acid glycine. Since the linear peptide Ser(99) to Glu(116) had no effect according to the invention (Hribar M. et al., Eur. J. Immunol. (1999), Vol. 29, 3105-3111; Braun C., J. Immunol. (2005), 175: 3402-3408; Fukuda N. et al. Am J Physiol Lung Cell Mol Physiol (2001) 280: L1258-L1265), position Glu(116) had to be replaced additionally by the amino acid cysteine in order to maintain the structure and in order to enable a ring closure between the two amino acids cysteine.

A disadvantage of the peptide described in WO00/09149 is that said peptide contains amino acid sequences which are artificial, that is to say, are not contained in TNF in this form.

Such a peptide provided with artificial structures is recognized as exogenous by the human immune system. A repeated or permanent administration of such a peptide in medicinal form may cause life-threatening immune reactions.

Surprisingly, it has now been found that a protein composed of parts of the amino acid sequence of the mature tumour necrosis factor (TNF) exhibits interesting biological properties, with such a protein containing no artificial amino acid sequences.

In one aspect, the present invention provides a reverse tumour necrosis factor protein, e.g., a protein which is composed N-terminally of one or several C-terminal parts, preferably of one part of the amino acid sequence of the mature tumour necrosis factor, and C-terminally of one or several N-terminal parts, preferably of one part of the amino acid sequence of the mature tumour necrosis factor, e.g., in the form of a fusion protein.

The mature tumour necrosis factor (TNF), as used herein, is preferably the human mature tumour necrosis factor.

A protein provided according to the present invention is herein referred to also as a "protein according to (of) the present invention".

Parts of the amino acid sequence of the mature tumour necrosis factor (TNF) are herein referred to also as "structural elements of the tumour necrosis factor (TNF)".

In another aspect, the present invention provides a protein according to the present invention which is composed N-terminally of one or several C-terminal structural elements of the mature tumour necrosis factor and C-terminally of one or several N-terminal structural elements of the mature tumour necrosis factor, e.g., in the form of a fusion protein.

Structural elements of the mature tumour necrosis factor are defined in TABLE 1.

A protein according to the present invention includes a fusion protein composed of parts of the amino acid sequence of the human TNF as defined above, e.g., of structural elements of the TNF.

Furthermore, it has been found that it is particularly advantageous if a protein according to the present invention is derived N-terminally from the C-terminal structural elements β-Strand 6 to β-Strand 10, or β-Strand 8 to β-Strand 9, of the TNF, and C-terminally from the N-terminal structural elements β-Strand 2 to β-Strand 3, or β-Strand 3 of the TNF, e.g., with the proviso that at least two cysteine moieties are included.

According to the present invention, particularly suitable proteins comprising amino acid sequences

```
                                            SEQ ID:NO: 1
(NH2)Ala-Ile-Lys-Ser-Pro-Cys-Gln-Arg-Glu-Thr-Pro-
Glu-Gly-Ala-Glu-Ala-Lys-Gly-Gly-Cys-Pro-Ser-Thr-
His-Val(COOH);

SEQ ID:NO: 2
(NH2)Lys-Ser-Pro-Cys-Gln-Arg-Glu-Thr-Pro-Glu-Gly-
Ala-Glu-Ala-Lys-Gly-Gly-Cys-Pro-Ser(COOH),
and SEQ ID:NO: 3
(NH2)Cys-Gln-Arg-Glu-Thr-Pro-Glu-Gly-Ala-Glu-Ala-
Lys-Gly-Gly-Cys(COOH)
``` have been found.

In another aspect, the present invention provides a protein according to the present invention comprising amino acid sequence SEQ ID:NO:1, SEQ ID:NO:2 or SEQ ID:NO:3.

In a protein comprising amino acid sequence SEQ ID:NO 1, the N-terminal portion of the protein Ala(96) to Lys(112) is derived from the C-terminal structural elements β-Strand 6 to β-Strand 9 of the human TNF and the C-terminal portion Gly(68) to Val(74) is derived from the N-terminal structural elements β-Strand 2 and β-Strand 3 of the human TNF. Numerals (96), (112), (68) and (74) denote the positions of the amino acids in the human TNF.

In a protein comprising amino acid sequence SEQ ID:NO 2, the N-terminal portion of the protein Lys(98) to Lys(112) is derived from the C-terminal structural elements β-Strand 7 to β-Strand 9 of the human TNF and the C-terminal portion of the reverse fusion protein Gly(68) to Ser(71) is derived from the N-terminal structural element β-Strand 3 of the human TNF. Numerals (98), (112), (68) and (71) denote the positions of the amino acids in the human TNF.

In a protein comprising amino acid sequence SEQ ID:NO 3, the N-terminal portion of the protein Cys(101) to Lys(112) is derived from the C-terminal structural elements β-Strand 7 to β-Strand 9 of the human TNF and the C-terminal portion Gly(68) to Cys(69) is derived from the N-terminal structural element β-Strand 3 of the human TNF.

Furthermore, it has surprisingly been found that, in a protein according to the present invention, a ring closure is rendered possible, e.g., is provided, by a bond between two cysteine moieties, e.g., a ring closure by a bond between a cysteine moiety originating from the N-terminal amino acid sequence of the TNF and a cysteine moiety originating from the C-terminal amino acid sequence of the TNF; e.g., a ring closure by a disulfide bridge between the respective sulfur molecules of the two cysteine moieties.

In another aspect, the present invention provides a protein according to the present invention wherein a ring closure is rendered possible by a bond between two cysteine moieties, e.g., the protein is a cyclic protein due to the bond between two cysteine moieties.

In the proteins SEQ ID NO:1 to SEQ ID NO:9, a ring closure occurs between the two cysteines which correspond to cysteines Cys(101) and Cys(69) in the human TNF.

A disulfide bridge can be cleaved, for example, hydrolytically or enzymatically, and it depends on the ambient conditions whether a protein according to the present invention exists in a cyclic or non-cyclic form, for example, a protein according to the present invention can exist in a biological environment in a cyclic or non-cyclic form. A protein according to the present invention can exist both in a cyclic form, as described herein, and in a non-cyclic form (no disulfide bridge) and, in a pure isolated form, preferably exists in a cyclic form.

In the structure of the human TNF, no ring closure is formed by a disulfide bridge between the respective sulfur molecules of two cysteine moieties.

A protein according to the present invention can exist in free form or in the form of a salt, e.g., in the form of an acid addition salt such as an acetate salt or a trifluoroacetic acid salt, and, in a further aspect, the present invention provides a protein according to the present invention in the form of a salt.

A protein according to the present invention can be produced in a suitable manner, e.g., analogously to a known process, such as by chemical synthesis by means of peptide chemistry or using microbial processes, for example, as described herein.

It has turned out that a protein according to the present invention shows an interesting biological activity and thus can be used as a medicament.

In a further aspect, the present invention provides a protein according to the present invention for use as a medicament, e.g., the use of a protein according to the present invention as a medicament.

For example, biological examinations on human cells show that a protein according to the present invention, also in contrast to the (human) TNF, exhibits virtually no inflammatory or toxic properties. For the examination, human immune cells from the blood are mixed with protein according to the present invention at a small concentration and are incubated in a manner common in laboratories. Subsequently, marker proteins for inflammations are determined by conventional methods. Despite the addition of a protein according to the present invention, e.g., a protein of amino acid sequence SEQ ID NO:1, SEQ ID NO:2 or SEQ ID NO:3, such inflammatory proteins, such as, e.g., the inflammation marker Interleukin-6 (IL-6), cannot be detected.

In a further aspect, the present invention provides a process for preventing inflammations, e.g., for preventing the formation of inflammation markers such as IL-6 in the medical application of proteins derived from the tumour necrosis factor, e.g., from the human tumour necrosis factor, which is characterized in that a protein according to the present invention is used.

Furthermore, a method common in laboratories is to detect the activation of ion channels by means of patch-clamp experiments, and this is described, for example, in Clunes M. T. et al, J Physiol Volume 557, No. 3, 809-819 (Jun. 15, 2004). For patch-clamp examinations of ion channels, a glass cannula is stretched thin and filled with a neutral buffer solution. The glass cannula (patch-clamp pipette) is carefully pressed onto an intact epithelial cell. A piece of membrane is located below the pipette. An electrical resistance is thereby produced between the interior of the pipette and the external solution. An electrode attached to a sensitive amplifier dips into the pipette solution.

It now surprisingly turns out that a protein according to the present invention, such as a protein of amino acid sequence SEQ ID NO:1, SEQ ID NO:2 or SEQ ID NO:3, will activate epithelial ion channels, which is detectable by a variation in the electrical voltage versus the amperage.

For the simulation of an acute lung injury and for the formation of a pulmonary oedema, the lungs of laboratory animals, e.g., mice or rats, can be rinsed several times with an acidified saline solution in a manner common in laboratories (for example, according to Isik F. et al., Eur J Cardiothorac Surg (2005); 28: 301-305). The result is a decrease in lung function. If a protein according to the present invention, e.g., a protein of amino acid sequence SEQ ID NO:1, SEQ ID NO:2 or SEQ ID NO:3, is injected as a fog or in an aqueous solution into the lungs of the laboratory animals, a distinct improvement in the lung function will occur within 3 to 5 hours, as indicated by the increased oxygen content in the arterial blood. Thus, a protein according to the present invention can be used for the treatment of oedemas such as pulmonary oedemas.

In another aspect, the present invention provides a protein according to the present invention for the treatment of diseases associated with the lung function, e.g., the use of a protein according to the present invention for the manufacture of a medicament for the treatment of diseases associated with the lung function.

The treatment of diseases associated with the lung function includes, for example, the activation of epithelial ion channels, the improvement of the lung function and/or the treatment of oedemas such as pulmonary oedemas, the treatment
  of Acute Lung Injury, ALI,
  of Acute Respiratory Distress Syndrome, ARDS,
  of Severe Acute Respiratory Syndrome (SARS),
  of pneumonia,
  in case of multi-organ failure,
  in case of respiration-induced lung injuries, lung transplants, transfusion-associated lung injuries, therapeutical administration of IL-2 or asthma, e.g., the activation of epithelial ion channels, the improvement of the lung function and/or the treatment of oedemas such as pulmonary oedemas.

In another aspect, the present invention provides a process for the treatment of diseases associated with the lung function, which is characterized in that a sufficient amount of a protein according to the present invention is administered to a patient in need of such a treatment.

A patient, as used herein, includes mammals, e.g., humans.

A protein according to the present invention can be administered in the form of a pharmaceutical preparation.

In another aspect, the present invention provides a pharmaceutical preparation which is characterized in that it comprises a protein according to the present invention, e.g., in combination with at least one pharmaceutically acceptable adjuvant such as carriers or diluents, for example, fillers, binders, flow-conditioning agents, lubricants, flavouring agents, sugar or sweeteners, odorous substances, preservatives, substances having a stabilizing effect, humectants, emulsifiers, solubilizers, salts for regulating the osmotic pressure and/or buffer (mixtures).

The suitable amount of a protein according to the present invention for the treatment of diseases will of course depend strongly on different parameters, for example, the chemical nature and the pharmacokinetics of the protein used, the individual patient, the disease to be treated, the type of application, however, a successful daily dose for larger mammals includes, for example, an amount ranging from 0.0001 g to 1.5 g, e.g., from 0.001 mg/kg body weight to about 20 mg/kg body weight.

The application may occur enterally or parenterally and preferably occurs parenterally. A pharmaceutical preparation according to the present invention can be produced in a suitable manner, e.g., analogously to a known method, e.g., by mixing, granulation, coating, dissolution, lyophilization methods.

In the examples, the following abbreviations are used:
TFA salt salt of trifluoroacetic acid

EXAMPLE 1

Synthesis of a Protein Comprising Amino Acid Sequence SEQ ID NO:1

A protein comprising amino acid sequence SEQ ID NO:1 was synthesized fully automatically via Fmoc solid-phase synthesis in the following steps:

| Step | Process | Product |
|---|---|---|
| 1 | coupling of amino acids | peptide bound to the solid phase |
| 2 | splitting from the solid phase | peptide in solution |
| 3 | purification | purified peptide as a TFA-salt |
| 4 | purification/salt exchange/ oxidative cyclization | purified peptide as an acetate salt |
| 5 | analytical examination | purified peptide |

The cyclization was achieved by forming a disulfide bridge between the side chains of the amino acids cysteine (position 6) and cysteine (position 20). This is effected, for example, by oxygen oxidation of the sulfur atoms in the side chains of the cysteine (position 6) and of the cysteine (position 20), whereby a disulfide bridge is formed, which results in a ring closure.

Figure 1A:
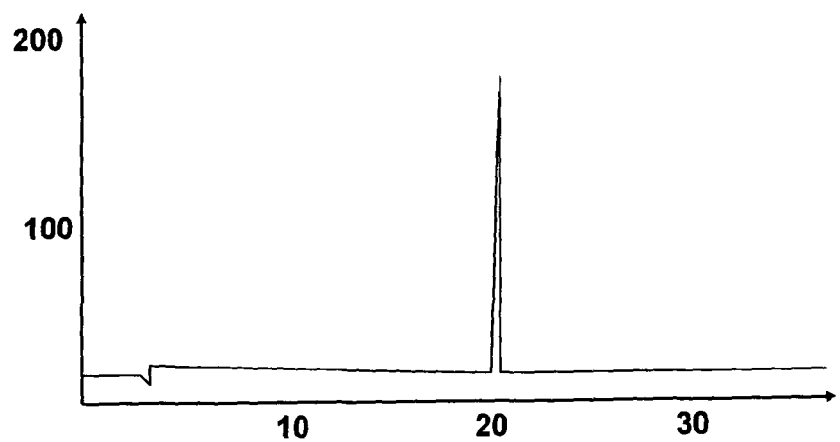
FIG. 1A shows the HPLC chromatogram of the protein comprising amino acid sequence SEQ ID NO:1. Units: y-axis: absorption in mV; x-axis: time in minutes.

Subsequently, the protein was examined via reverse HPLC, whereby the result as shown in FIG. 1A was obtained.

EXAMPLE 2

Synthesis of a Protein Comprising Amino Acid Sequence SEQ ID NO:2

A protein comprising amino acid sequence SEQ ID NO:2 was synthesized fully automatically via Fmoc solid-phase synthesis in the following steps:

| Step | Process | Product |
|---|---|---|
| 1 | coupling of amino acids | peptide bound to the solid phase |
| 2 | splitting from the solid phase | peptide in solution |
| 3 | purification | purified peptide as a TFA-salt |
| 4 | purification/salt exchange/ oxidative cyclization | purified peptide as an acetate salt |
| 5 | analytical examination | purified peptide |

The cyclization was achieved by forming a disulfide bridge between the side chains of the amino acids cysteine (position 4) and cysteine (position 18). This is effected, for example, by oxygen oxidation of the sulfur atoms in the side chains of the cysteine (position 4) and of the cysteine (position 18), whereby a disulfide bridge is formed, which results in a ring closure.

Figure 1B:
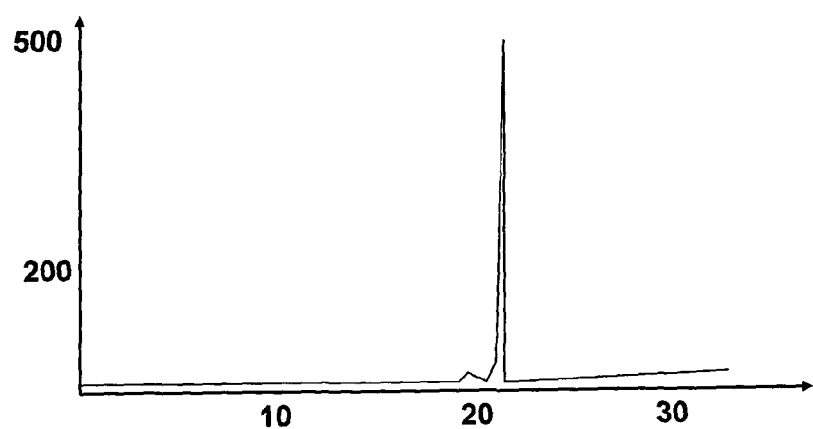
FIG. 1B shows the HPLC chromatogram of the protein comprising amino acid sequence SEQ ID NO:2. Units: y-axis: absorption in mAU; x-axis: time in minutes.

Subsequently, the protein was examined via reverse HPLC, whereby the result as shown in FIG. 1B was obtained:

EXAMPLE 3

Synthesis of a Protein Comprising Amino Acid Sequence SEQ ID NO:3

A protein comprising amino acid sequence SEQ ID NO:3 was synthesized fully automatically via Fmoc solid-phase synthesis in the following steps:

| Step | Process | Product |
|---|---|---|
| 1 | coupling of amino acids | peptide bound to the solid phase |
| 2 | splitting from the solid phase | peptide in solution |
| 3 | purification | purified peptide as a TFA-salt |
| 4 | purification/salt exchange/ oxidative cyclization | purified peptide as an acetate salt |
| 5 | analytical examination | purified peptide |

The cyclization was achieved by forming a disulfide bridge between the side chains of the amino acids cysteine (position 1) and cysteine (position 15). This is effected, for example, by oxygen oxidation of the sulfur atoms in the side chains of the cysteine (position 1) and of the cysteine (position 15), whereby a disulfide bridge is formed, which results in a ring closure.

Figure 1C:
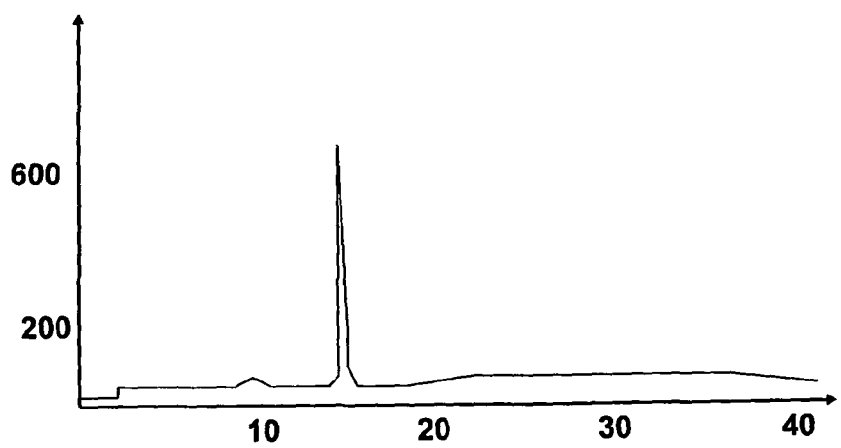
FIG. 1C shows the HPLC chromatogram of the protein comprising amino acid sequence SEQ ID NO:3. Units: y-axis: absorption in mAU; x-axis: time in minutes.

Subsequently, the protein was examined via reverse HPLC, whereby the result as shown in FIG. 1C was obtained:

EXAMPLE 4

Cell Culture

The electrophysiological experiments were performed on human A549 cells (ATTC No. CCL-185). A549 cells are human lung epithelial cells which are involved in the diffusion of water and electrolytes in the lungs.

The cells were suspended in DMEM-F-12 medium with 1% penicillin-streptomycin and 10% fetal calf serum, transferred into plastic cell culture vessels and cultivated in the incubator with 95% air and 5% $CO_2$ at 37° C. The medium was changed 2 to 3 times per week. The cells double within approx. 22 hours and a cell concentration of more than $7 \times 10^4$ cells per $cm^2$ was not exceeded.

EXAMPLE 5

Activation of Ion Channels of Human Epithelial Cells by Proteins Comprising Amino Acid Sequence SEQ ID NO:1, SEQ ID NO:2 or SEQ ID NO:3

Macroscopic currents and single-channel currents were discharged from A549 cells in the "whole cell" and "cell-attached" configuration of the "patch-clamp" technique (Hamill et al, Pflugers Arch. 1981, 391(2):85-100, 1981). For the current dissipations in the "whole cell" configuration, the following bath and electrode solutions were used:

Bath solution: 135 mM sodium methane sulfonate, 10 mM NaCl, 2.7 mM KCl, 1.8 mM CaCl2, 2 mM MgCl2, 5.5 mM glucose, and 10 mM HEPES, pH 7.4.

Electrode solution: 120 mM potassium methyl sulfonate, 15 mM KCl, 6 mM NaCl, 1 mM Mg2ATP, 2 mM Na3ATP, 10 mM HEPES, and 0.5 mM EGTA (pH 7.2).

The cover slips with the cells cultivated thereon were transferred into a test bath with a capacity of 1 ml, fixed on the microscope table (Axiovert 100, 400-fold magnification), and the cells were superfused with the above-described bath solution. Thereupon, the current was discharged from a suitable cell (which adheres to the cover slip). For this purpose, a microelectrode filled with an electrolyte solution (glass capillary with a defined, heat-polished tip opening of about 1-3 μm, corresponding to a resistance of the electrode tip of 3-5Ω) was placed on the cell and the membrane was sucked in so that a "Gigaohm seal" was formed between the membrane and the electrode in order to minimize the leakage current. In the "cell-attached" configuration, the current can be measured through individual ion channels beneath the electrode tip. In the "whole cell" configuration, the membrane was penetrated beneath the electrode tip so that the current flowing through all ion channels of the cell could be measured. The dissipation of the macroscopic currents can also be performed by means of the "perforated patch clamp" technique. For the "whole cell" dissipation, the ionophore amphotericin was added to the pipette solution, whereby the membrane became permeable beneath the tip opening and the currents could be discharged in the "whole cell" configuration. Upon obtaining a Gigaohm seal, a defined membrane retaining potential was applied via a pre-amplifier (CV-4 Headstage, Axon Instruments) and an amplifier (Axopatch 1D, Axon Instr.) and the current thereby flowing through the ion channels was measured.

The pulse protocol consisted of a hyperpolarization to −100 mV for 1 s at an interval of 5 s. In further consequence, the membrane was finally depolarized as far as to +100 mV in steps of 20 mV. Said protocol was carried out by adding synthetic proteins comprising amino acid sequence SEQ ID NO:1, SEQ ID NO:2 or SEQ ID NO:3 as well as with the sodium channel inhibitor amiloride. The current dissipations thus obtained were stored and analyzed by means of the program PCLAMP 6.0. For this purpose, the current dissipations obtained in the presence of amiloride were subtracted from the currents recorded earlier so that the amiloride-sensitive sodium current through the epithelial sodium channels could be determined.

Figure 2A:
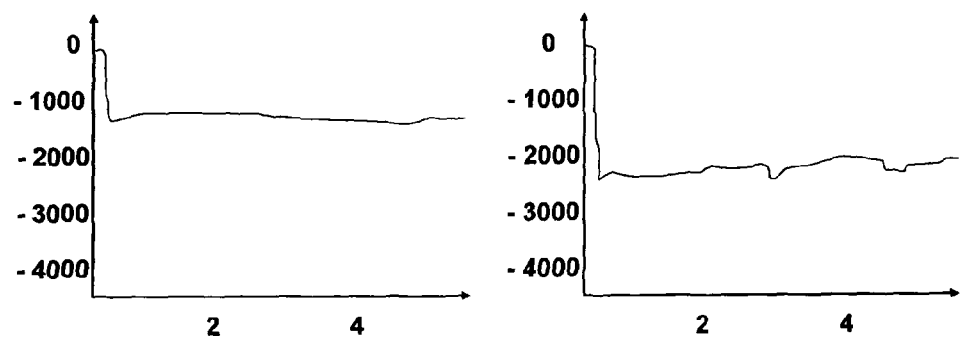
FIG. 2A, right-hand image shows the activation of sodium ion channels by a protein of amino acid sequence SEQ ID NO:1 (referred to as "sequence 1" in the figure), detected by patch clamp. For comparison, left-hand image in FIG. 2A without a protein. Units: y-axis: amperage in pA; x-axis: time in seconds.
Figure 2B:
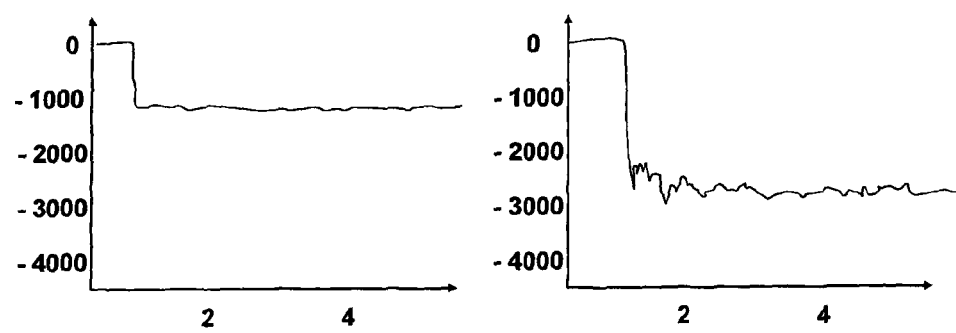
FIG. 2B, right-hand image shows the activation of sodium ion channels by a protein of amino acid sequence SEQ ID NO:2 (referred to as "sequence 2" in the figure), detected by patch clamp. For comparison, left-hand image in FIG. 2B without a protein. Units: y-axis: amperage in pA; x-axis: time in seconds.
Figure 2C:
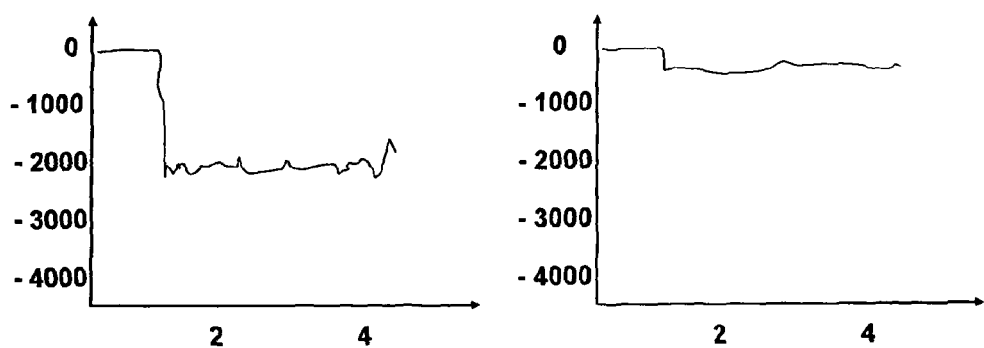
FIG. 2C, left-hand image shows the activation of sodium ion channels by a protein of amino acid sequence SEQ ID NO:3, detected by patch clamp, in comparison to the inhibition of ion channels by 10 µM amiloride (right-hand image). Units: y-axis: amperage in pA; x-axis: time in seconds.

The results in which the activation of the sodium ion channels by the proteins comprising amino acid sequences SEQ ID NO:1, SEQ ID NO:2 and SEQ ID NO:3 is shown are evident from FIG. 2A, FIG. 2B and FIG. 2C.

EXAMPLE 6

Experimental Animal Study Pulmonary Oedema

Male Wistar rats (weighing from 250 g to 350 g) are anesthetized with Rompun® (0.02 ml/100 g) and Ketavet® (0.1 ml/100 g). The respiration is done with a cycle of 72 blows/minute, with an inhalation time of 0.2 seconds and an exhalation time of 0.5 seconds. The body temperature ranges, on average, from 37° C. to 39° C. Under normal conditions, the PaO2 (arterial oxygen partial pressure) ranges from 500 to 550 mm Hg.

For the simulation of an acute lung injury and for the formation of a pulmonary oedema, the lungs are rinsed 7 to 9 times with an acidified saline solution (pH 5).

After one hour, the proteins comprising amino acid sequence SEQ ID NO:1, SEQ ID NO:2 or SEQ ID NO:3, dissolved in sterile saline solution, are, in each case, administered intratracheally as a fog (maximum volume administered: 0.5 ml).

At intervals of 60 minutes each, arterial blood (0.1 ml) is withdrawn from the animals, and the oxygen content is determined in % relative to the normal value.

Figure 3A:
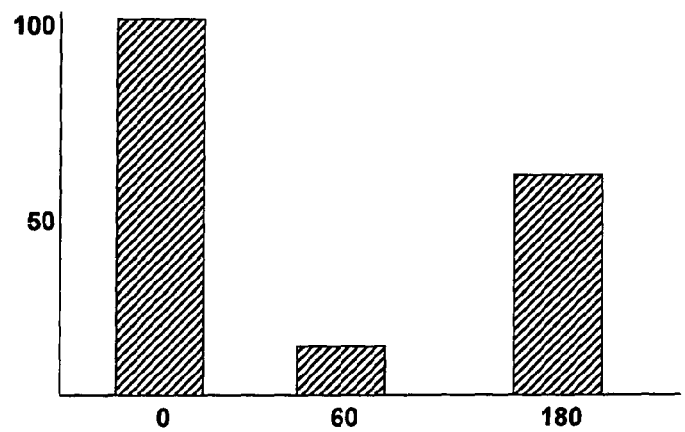
FIG. 3A shows the increase in the oxygen content in the arterial blood upon administration of a protein comprising amino acid sequence SEQ ID NO:1. Units: y-axis: oxygen content in %; x-axis: measuring time in minutes.
Figure 3B:
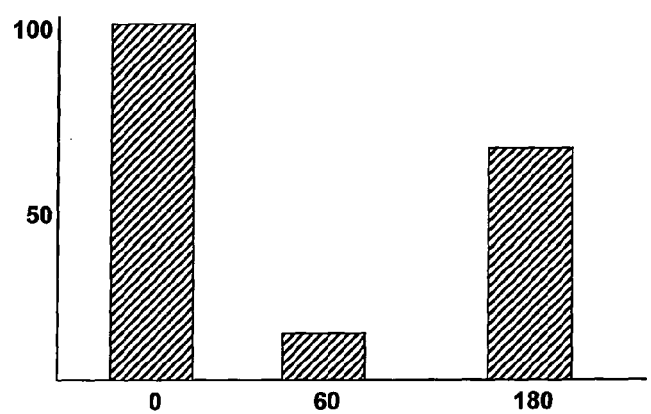
FIG. 3B shows the increase in the oxygen content in the arterial blood upon administration of a protein comprising amino acid sequence SEQ ID NO:2. Units: y-axis: oxygen content in %; x-axis: measuring time in minutes.
Figure 3C:
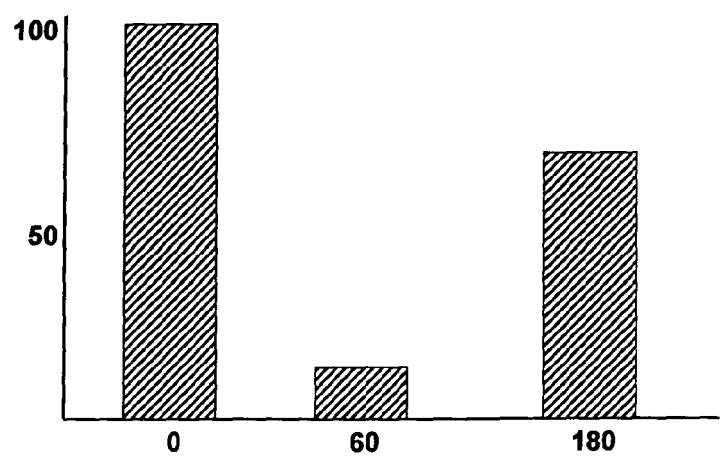
FIG. 3C shows the increase in the oxygen content in the arterial blood upon administration of a protein comprising amino acid sequence SEQ ID NO:3. Units: y-axis: oxygen content in %; x-axis: measuring time in minutes.

After administering a protein comprising amino acid sequence SEQ ID NO:1, SEQ ID NO:2 or SEQ ID NO:3, the oxygen content in the blood is increased, as is evident from FIG. 3A, FIG. 3B or FIG. 3C, see also Example 7.

EXAMPLE 7

Improvement of the Lung Function

The verification of the stimulating effect of a protein according to the present invention, e.g., of a protein comprising amino acid sequence SEQ ID NO:1, SEQ ID NO:2 or SEQ ID NO:3, on the lung function is made via experimental animal studies in which a pulmonary oedema is induced. The experimental procedure is described in Example 6. In each case, 5 animals are used for objectifying the measured values.

For the intratracheal inhalation, 125 µg protein are, in each case, dissolved in 150 mM saline solution pH 7.3. The oxygen content of the arterial blood is measured immediately before rinsing the lungs, 60 minutes after rinsing the lungs and 180 minutes after rinsing the lungs.

The oxygen content immediately before rinsing the lungs is determined to be 100%. 60 minutes after the respective final lung rinsing, the oxygen content in the blood amounts to, on average, only 20%. Within 3 hours, the percentage oxygen content rises to values of 60% when the treatment occurs with a protein comprising amino acid sequence SEQ ID NO:1, 63% when the treatment occurs with a protein comprising amino acid sequence SEQ ID NO:2, and 70%, respectively, when the treatment occurs with a protein comprising amino acid sequence SEQ ID NO:3.

Without addition of protein, no improvement in the lung function (oxygen content 20%) will occur within 180 minutes after the lung rinsing.

The results are illustrated in

FIG. 3A for a protein comprising amino acid sequence SEQ ID NO:1,

FIG. 3B for a protein comprising amino acid sequence SEQ ID NO:2,

FIG. 3C for a protein comprising amino acid sequence SEQ ID NO:3.

EXAMPLE 8

Determination of Inflammatory Parameters

Fresh human blood has a very sensitive reaction to pro-inflammatory molecules, among other things, with a release of the inflammation marker Interleukin-6 (IL-6). For determining the pro-inflammatory reaction, samples of human fresh blood with different concentrations of the protein comprising amino acid sequence SEQ ID NO:3 were incubated at the following concentrations: 10 µg/ml, 3 µg/ml, 1 µg/ml. After an incubation of 24 hours at 37° C., the inflammation marker Interleukin-6 was quantitatively determined in the solution via ELISA. LPS served as a positive control.

In doing so, the measured data, which are indicated in TABLE 2 and which show the influence of the protein comprising amino acid sequence SEQ ID NO:3 in comparison to LPS, were obtained.

TABLE 2

| Concentration of protein and LPS, respectively | Protein SEQ ID NO: 3 | Positive control "LPS" |
|---|---|---|
| | Concentration of Interleukin-6 (pg/ml) (average of three measurements) | |
| without addition of protein (normal blood value) | less than 0.5 | less than 0.5 |
| 10 µg/ml | less than 0.5 | 195.640 |
| 1 µg/ml | less than 0.5 | 108.370 |
| 3 nµg/ml | less than 0.5 | 34.867 |
| 1 nµg/ml | less than 0.5 | not determined |

The measured data in TABLE 2 show that virtually no inflammation marker IL-6 is released by an incubation of human fresh blood with a protein of amino acid sequence SEQ ID NO:3 and that hence no inflammatory reaction is triggered. In contrast, an incubation with LPS as a positive control causes a strong release of the inflammation marker Interleukin-6.

The invention claimed is:

1. A protein selected from the amino acid sequences:
SEQ ID:NO: 1
(NH$_2$)Ala-Ile-Lys-Ser-Pro-Cys-Gln-Arg-Glu-Thr-Pro-Glu-Gly-Ala-Glu-Ala-Lys-Gly-Gly-Cys-Pro-Ser-Thr-His-Val(COOH);
SEQ ID:NO: 2
(NH$_2$)Lys-Ser-Pro-Cys-Gln-Arg-Glu-Thr-Pro-Glu-Gly-Ala-Glu-Ala-Lys-Gly-Gly-Cys-Pro-Ser(COOH); and
SEQ ID:NO: 3
(NH$_2$)Cys-Gln-Arg-Glu-Thr-Pro-Glu-Gly-Ala-Glu-Ala-Lys-Gly-Gly-Cys(COOH), wherein the protein includes a ring closure by a bond between two cysteine moieties.

2. A medicament comprising a protein according to claim 1.

3. A medicament according to claim 2, wherein the protein is present in a sufficient amount for the improvement of lung function in one or more diseases selected from pulmonary oedemas, Acute Lung Injury (ALI), Acute Respiratory Distress Syndrome (ARDS), Severe Acute Respiratory Syndrome (SARS), pneumonia, multi-organ failure, respiration-induced lung injuries, injuries relating to lung transplants, transfusion-associated lung injuries, and asthma.

4. A medicament according to claim 3, wherein the protein is present in a sufficient amount for improving lung function in pulmonary oedema.

5. A method for the improvement of lung function in one or more diseases selected from pulmonary oedemas, Acute Lung Injury (ALI), Acute Respiratory Distress Syndrome (ARDS), Severe Acute Respiratory Syndrome (SARS), pneumonia, multi-organ failure, respiration-induced lung injuries, injuries relating to lung transplants, transfusion-associated lung injuries, and asthma, the method comprising:
administering a protein according to claim 1 to a patient in need thereof.

6. A method of treating pulmonary oedema comprising administering to a subject in need of such treatment a sufficient amount of a protein according to claim 1.

7. A pharmaceutical preparation comprising a protein according to claim 1.

8. A protein according to claim 1 in the form of a salt.

9. A method of treating pulmonary oedema comprising administering to a subject in need of such treatment a sufficient amount of a protein according to claim 8.

10. A pharmaceutical preparation comprising a protein according to claim 8.

11. A medicament comprising a protein according to claim 8.

12. A medicament according to claim 11, wherein the protein is present in a sufficient amount for the improvement of lung function in one or more diseases selected from pulmonary oedemas, Acute Lung Injury (ALI), Acute Respiratory Distress Syndrome (ARDS), Severe Acute Respiratory Syndrome (SARS), pneumonia, multi-organ failure, respiration-induced lung injuries, injuries relating to lung transplants, transfusion-associated lung injuries, and asthma.

13. A medicament according to claim 11, wherein the protein is present in a sufficient amount for improving lung function in pulmonary oedema.

14. A method for the improvement of lung function in one or more diseases selected from pulmonary oedemas, Acute Lung Injury (ALI), Acute Respiratory Distress Syndrome (ARDS), Severe Acute Respiratory Syndrome (SARS), pneumonia, multi-organ failure, respiration-induced lung injuries, injuries relating to lung transplants, transfusion-associated lung injuries, and asthma, the method comprising:
administering a protein according to claim 8 to a patient in need thereof.

* * * * *

UNITED STATES PATENT AND TRADEMARK OFFICE
CERTIFICATE OF CORRECTION

| | | |
|---|---|---|
| PATENT NO. | : 8,372,799 B2 | Page 1 of 1 |
| APPLICATION NO. | : 12/747741 | |
| DATED | : February 12, 2013 | |
| INVENTOR(S) | : Fischer et al. | |

It is certified that error appears in the above-identified patent and that said Letters Patent is hereby corrected as shown below:

In the Specification

<u>Column 7</u>
Line 4, change "salt salt" to --salt: salt--

Signed and Sealed this
Thirteenth Day of August, 2013

Teresa Stanek Rea
*Acting Director of the United States Patent and Trademark Office*

SEQUENCE LISTING

<160> NUMBER OF SEQ ID NOS: 4

<210> SEQ ID NO 1
<211> LENGTH: 25
<212> TYPE: PRT
<213> ORGANISM: Artificial
<220> FEATURE:
<223> OTHER INFORMATION: modified protein derived from the tumour necrosis factor (TNF)

<400> SEQUENCE: 1

Ala Ile Lys Ser Pro Cys Gln Arg Glu Thr Pro Glu Gly Ala Glu
1               5                   10                  15

Ala Lys Gly Gly Cys Pro Ser Thr His Val
            20                  25

<210> SEQ ID NO 2
<211> LENGTH: 20
<212> TYPE: PRT
<213> ORGANISM: Artificial
<220> FEATURE:
<223> OTHER INFORMATION: modified protein derived from the tumour necrosis factor

<400> SEQUENCE: 2

Lys Ser Pro Cys Gln Arg Glu Thr Pro Glu Gly Ala Glu Ala Lys
1               5                   10                  15

Gly Gly Cys Pro Ser
            20

<210> SEQ ID NO 3
<211> LENGTH: 15
<212> TYPE: PRT
<213> ORGANISM: Artificial
<220> FEATURE:
<223> OTHER INFORMATION: modified protein derived from the tumour necrosis factor

<400> SEQUENCE: 3

Cys Gln Arg Glu Thr Pro Glu Gly Ala Glu Ala Lys Gly Gly Cys
1               5                   10                  15

<210> SEQ ID NO 4
<211> LENGTH: 157
<212> TYPE: PRT
<213> ORGANISM: Homo sapiens

<400> SEQUENCE: 4

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

```
Pro Trp Tyr Glu Pro Ile Tyr Leu Gly Gly Val Phe Gln Leu Glu Lys
    115             120                 125
Gly Asp Arg Leu Ser Ala Glu Ile Asn Arg Pro Asp Tyr Leu Asp Phe
    130             135                 140
Ala Glu Ser Gly Gln Val Tyr Phe Gly Ile Ile Ala Leu
145             150             155
```